(12) United States Patent
Lev et al.

(10) Patent No.: US 6,952,855 B2
(45) Date of Patent: Oct. 11, 2005

(54) AUTOMATIC ELECTRIC TOOTHBRUSH

(75) Inventors: Mordechai Lev, Northville, MI (US); Roman S. Ferber, West Bloomfield, MI (US); John E. Nemazi, Bloomfield Hills, MI (US)

(73) Assignee: HoMedics, Inc., Commerce Township, MI (US)

( * ) Notice: Subject to any disclaimer, the term of this patent is extended or adjusted under 35 U.S.C. 154(b) by 412 days.

(21) Appl. No.: 10/203,692

(22) PCT Filed: Jun. 28, 2002

(86) PCT No.: PCT/US02/20458

§ 371 (c)(1),
(2), (4) Date: Aug. 13, 2002

(87) PCT Pub. No.: WO03/002017

PCT Pub. Date: Jan. 9, 2003

(65) Prior Publication Data

US 2003/0135940 A1 Jul. 24, 2003

Related U.S. Application Data

(60) Provisional application No. 60/302,010, filed on Jun. 29, 2001.

(51) Int. Cl.[7] .............................................. A61C 17/22
(52) U.S. Cl. .................... 15/28; 15/22.1; 200/42.01; 200/61.42; 200/61.58 R
(58) Field of Search ................. 200/512, 600, 200/42.01, 52 R, 61.41, 61.42, 61.58 R, 61.85, 332.3, 511; 15/22.1, 22.2, 22.3, 22.4, 23, 28

(56) References Cited

U.S. PATENT DOCUMENTS

| | | | | |
|---|---|---|---|---|
| 3,675,330 A | * | 7/1972 | Drapen et al. | ................. 433/99 |
| 3,699,952 A | * | 10/1972 | Waters et al. | ................. 601/18 |
| 3,848,336 A | * | 11/1974 | Copeland | ..................... 433/99 |
| 3,859,684 A | * | 1/1975 | Moskwinski | .................... 15/23 |
| 3,939,599 A | * | 2/1976 | Henry et al. | .................. 433/99 |
| 4,192,035 A | * | 3/1980 | Kuris | .......................... 15/22.1 |
| 4,458,702 A | * | 7/1984 | Grollimund | ................. 132/322 |
| 4,882,801 A | * | 11/1989 | Benz | ............................. 15/23 |
| 5,105,499 A | | 4/1992 | Dirksing | |
| 5,146,645 A | | 9/1992 | Dirksing | |
| 5,282,291 A | | 2/1994 | Spieler et al. | |
| 5,355,544 A | | 10/1994 | Dirksing | |
| 5,453,644 A | * | 9/1995 | Yap et al. | .................... 307/116 |
| 5,493,747 A | * | 2/1996 | Inakagata et al. | ............ 15/22.1 |
| 5,502,861 A | | 4/1996 | Spieler et al. | |
| 5,577,285 A | | 11/1996 | Drossler | |
| 5,625,916 A | | 5/1997 | McDougall | |
| 5,680,666 A | | 10/1997 | Ra | |
| 5,836,030 A | | 11/1998 | Hazeu et al. | |
| 5,901,397 A | | 5/1999 | Hafele et al. | |
| 6,067,688 A | | 5/2000 | West | |
| 6,178,579 B1 | | 1/2001 | Blaustein et al. | |
| 6,189,693 B1 | | 2/2001 | Blaustein et al. | |
| 6,195,828 B1 | | 3/2001 | Fritsch | |
| 6,237,178 B1 | | 5/2001 | Krammer et al. | |
| 6,308,358 B2 | | 10/2001 | Gruber et al. | |
| 6,308,359 B2 | | 10/2001 | Fritsch et al. | |
| 6,327,734 B1 | | 12/2001 | Meginniss, III et al. | |

FOREIGN PATENT DOCUMENTS

DE    4012413    * 10/1991

* cited by examiner

*Primary Examiner*—Mark Spisich
(74) *Attorney, Agent, or Firm*—Brooks Kushman P.C.

(57) ABSTRACT

An motorized electric toothbrush (10) includes a removable brush head (16) and a switch (12) that allows the toothbrush (10) to be used in an "automatic" mode. The "automatic" mode provides for intermittent motorized operation, such that when the brush head (16) contacts the operator's teeth, a second switch (20) is automatically actuated and the motor (14) engaged. The brush head (16) is easily removed for replacement when the bristles become worn or allow use of the toothbrush (10) by multiple users.

8 Claims, 10 Drawing Sheets

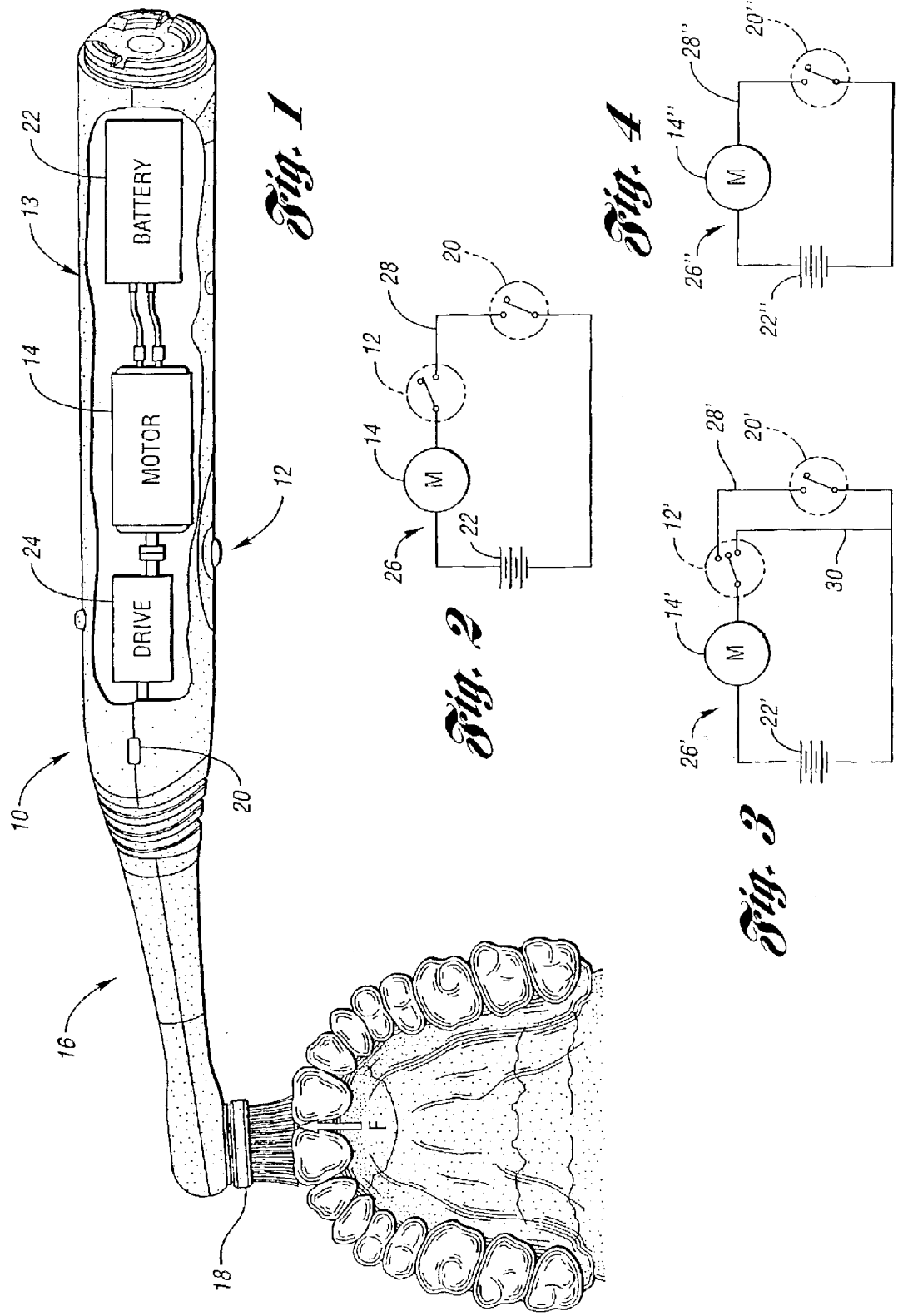

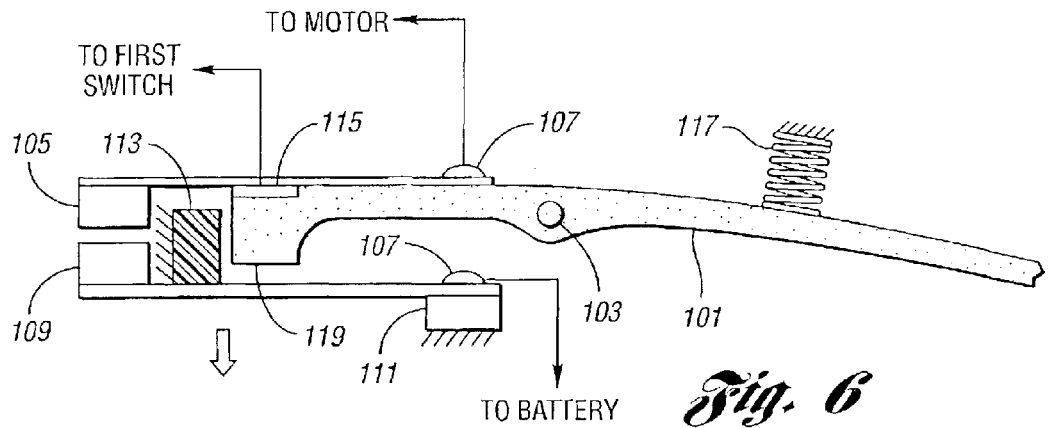
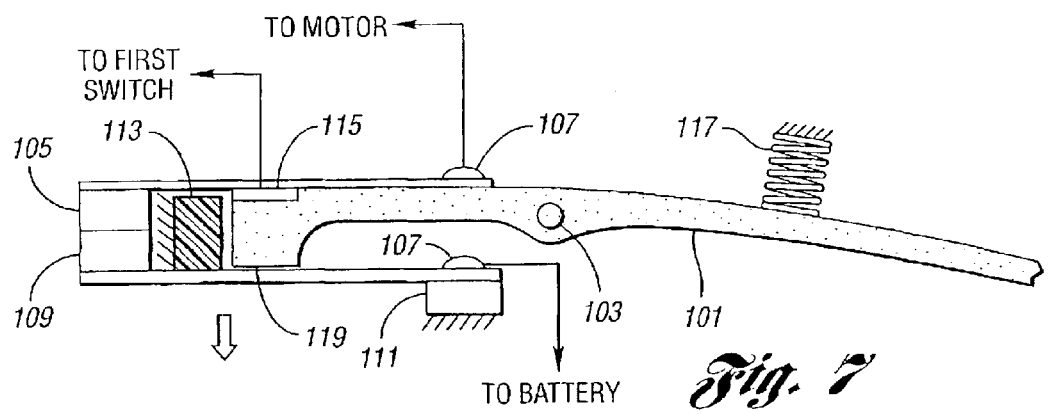
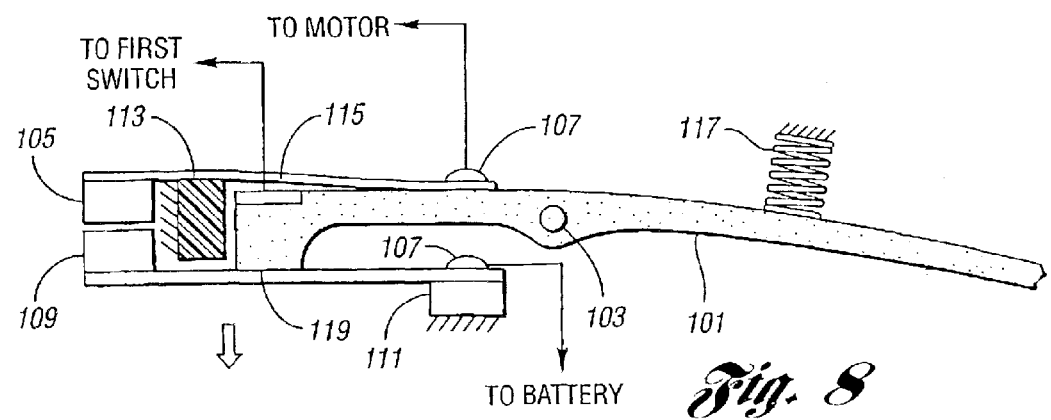

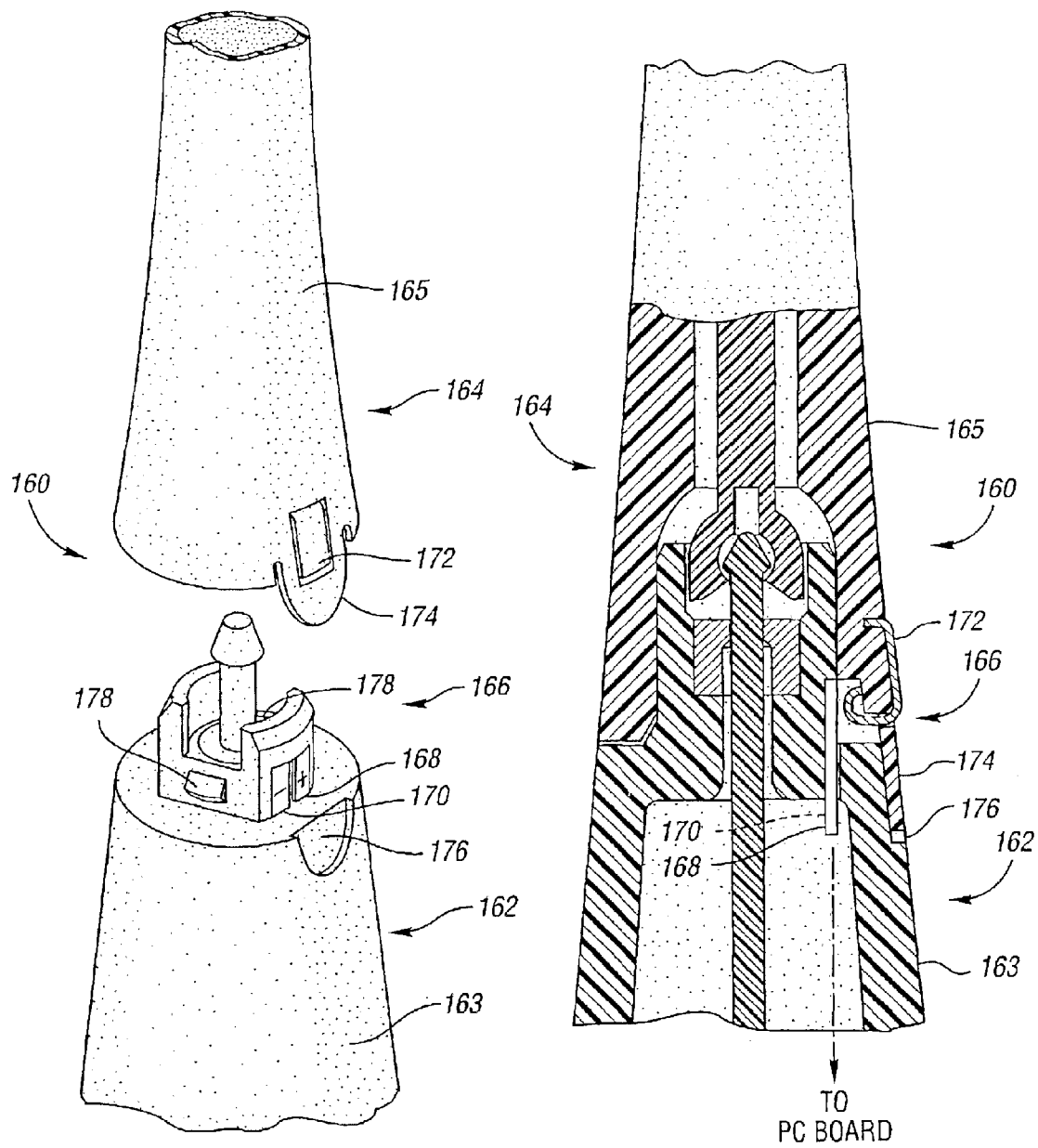

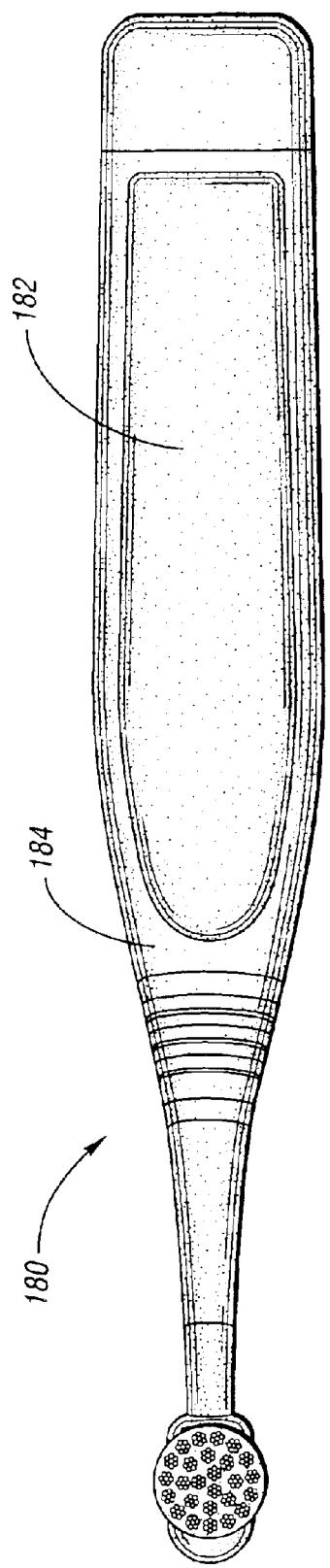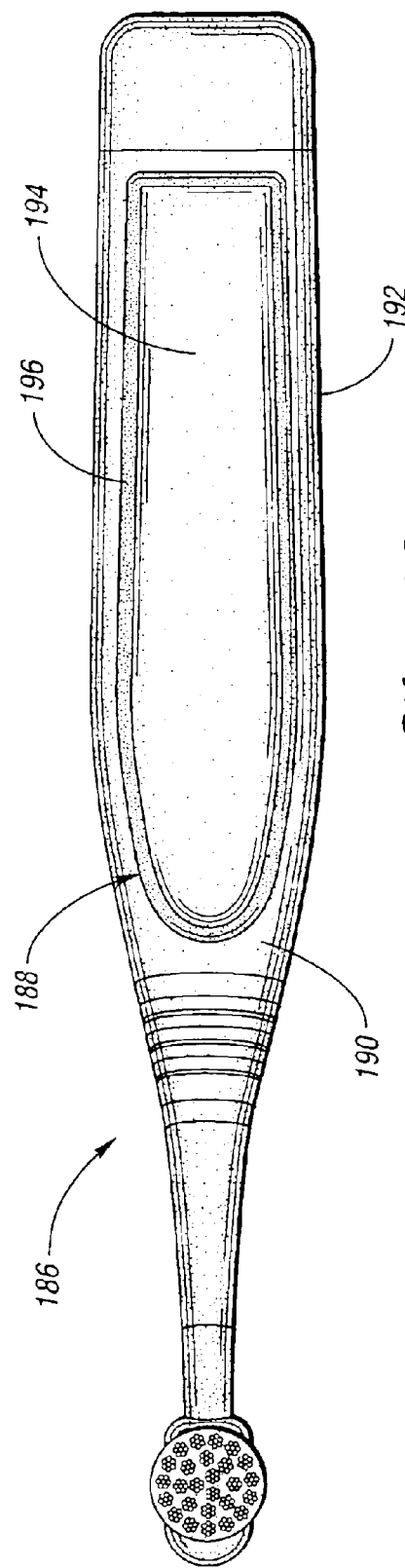

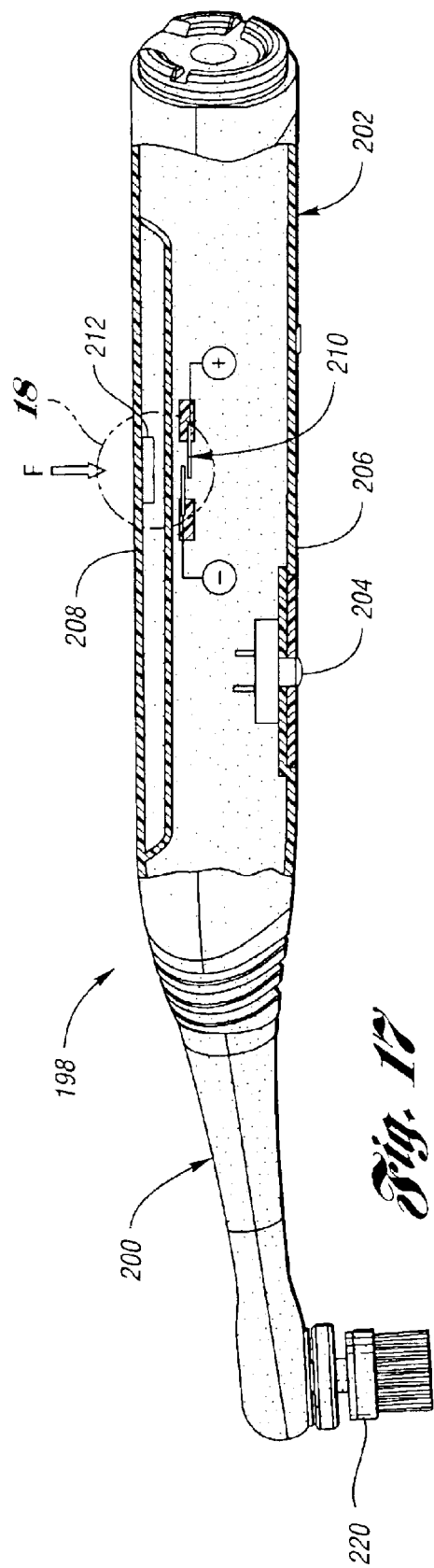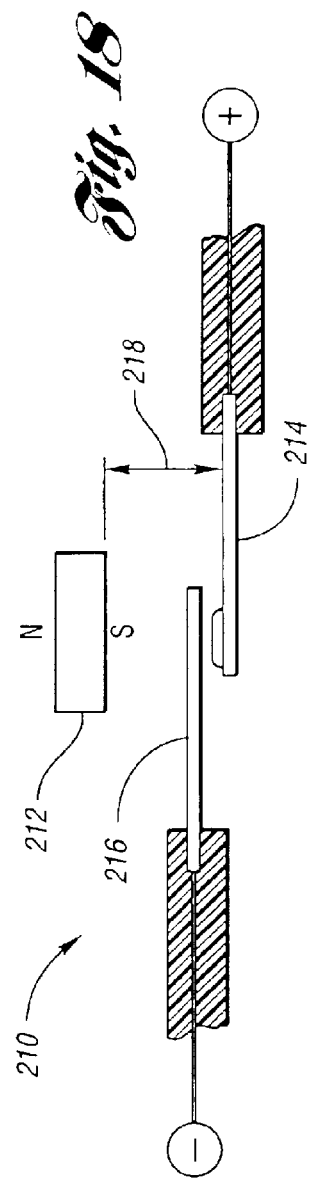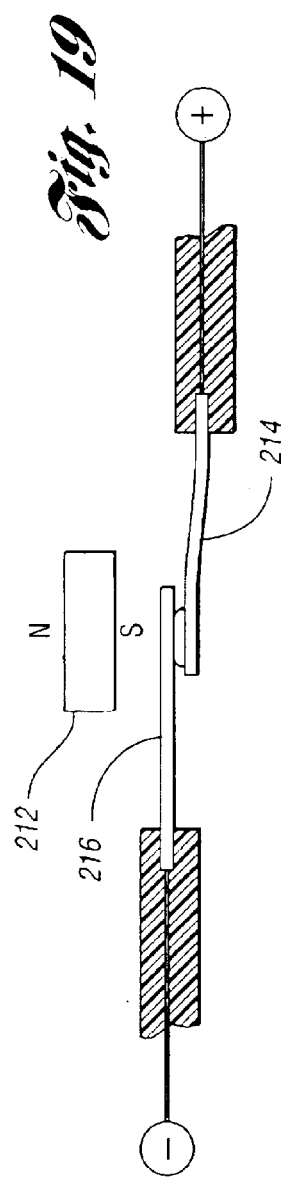

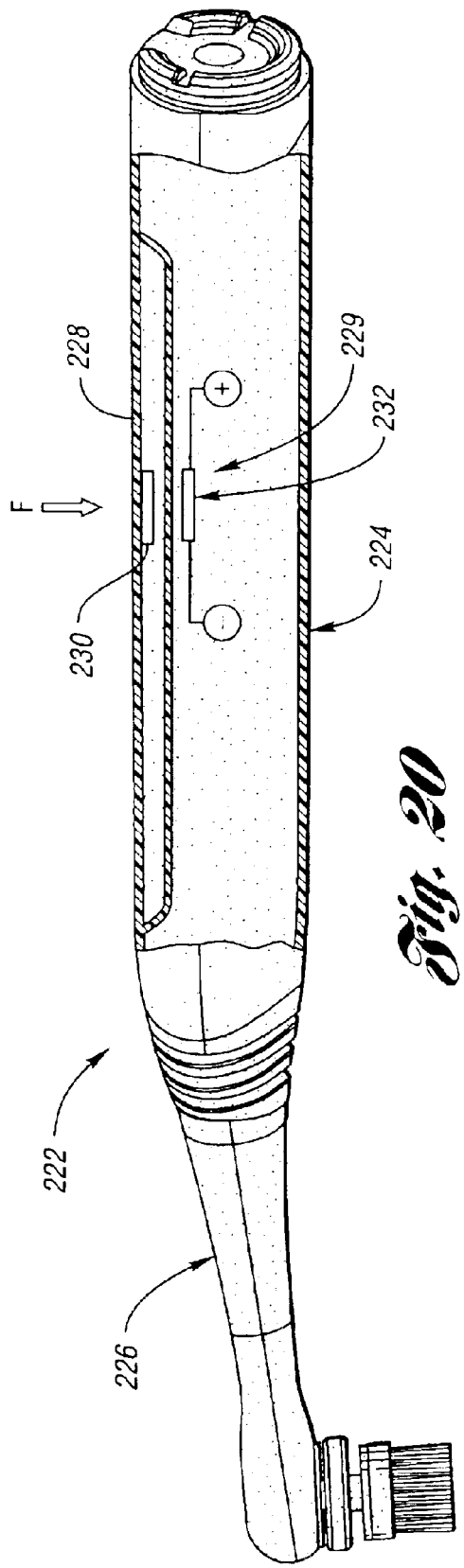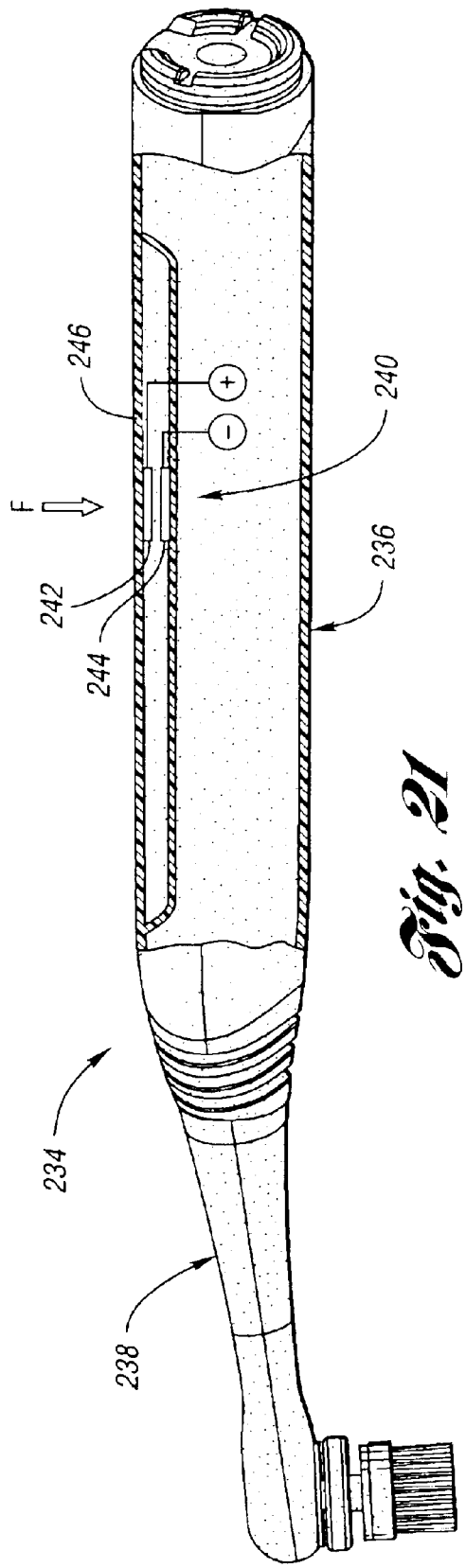

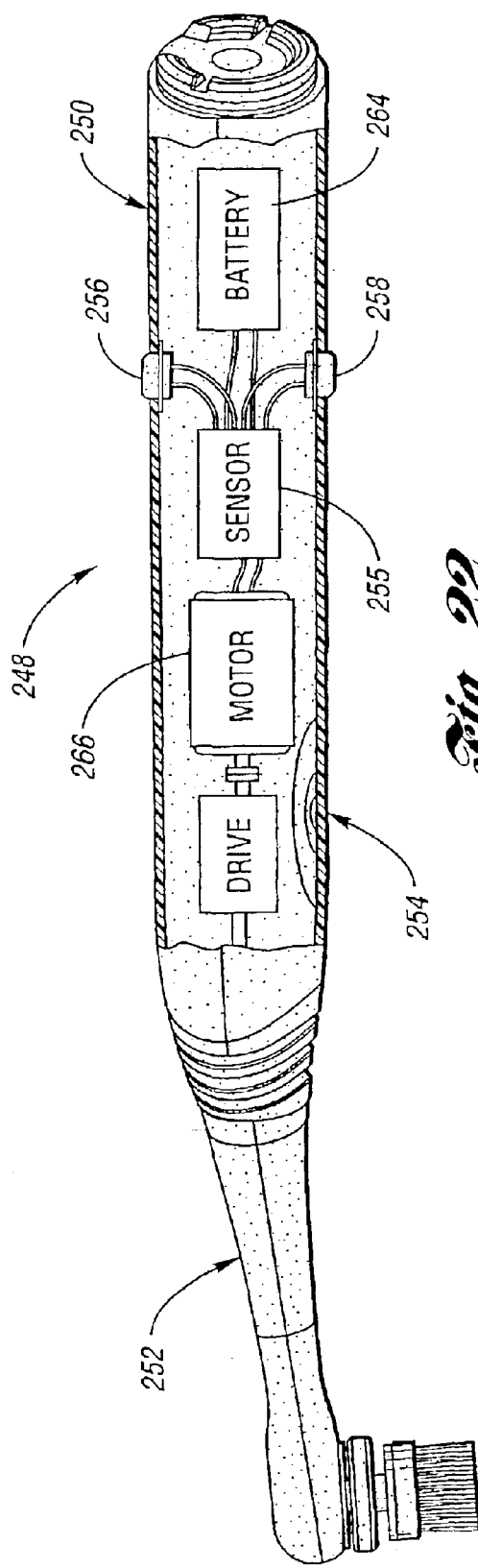
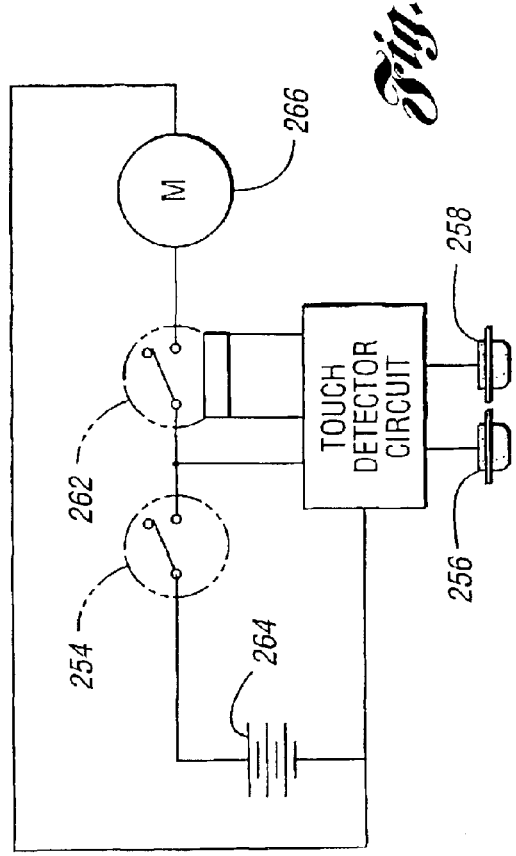
Fig. 22
Fig. 23

AUTOMATIC ELECTRIC TOOTHBRUSH

CROSS-REFERENCE TO RELATED APPLICATION

This application is the U.S. national phase of PCT application number PCT/US02/20458, filed Jun. 28, 2002, which further claims the benefit of U.S. provisional application Ser. No. 60/302,010, filed Jun. 29, 2001.

BACKGROUND OF THE INVENTION

1. Field of the Invention

The present invention relates to a motorized electric toothbrush having an automatic mode of operation.

2. Background Art

Use of motorized electric toothbrushes used as an aid in cleansing teeth is well known. Typically these toothbrushes employ rotating, reciprocating, or oscillating motion, or a combination thereof, to effectuate the cleaning process.

A feature commonly found on these toothbrushes is an on/off switch located on or near the handle portion of the toothbrush. The primary feature of such a switch is that it remains either in the "on" position or the "off" position until the user manually changes it. With such a switch, the user has a limited number of choices. The toothbrush motor can be engaged prior to the brush head being placed in the mouth, or the user can wait until the brush head is placed within the mouth before engaging the motor. Both of these choices may have undesirable consequences. When the user engages the motor prior to placing the brush head in the mouth, the rapid movement of brush head may cause the toothpaste to be shaken off the bristles. Conversely, if the user waits until the brush head is inside the mouth, and in particular in contact with the teeth, it may be difficult to engage the switch, depending on its position relative to the user's hand.

Another feature found on some motorized electric toothbrushes is a removable brush head section. This allows the brush head section to be replaced when the bristles become worn, and also allows the same toothbrush to be shared by multiple users. Typically, a removable brush head section attaches to the toothbrush handle and contains linkages to transfer mechanical power from the motor to a bristle head. Different types of attachments and linkages are known in the art, with particular mechanisms chosen to achieve particular results. For example, U.S. Pat. No. 6,308,359 issued to Fritsch et al. on Oct. 30, 2001 describes a motorized electric toothbrush having a removable brush section with an attachment mechanism intended to reduce noise and vibrations. Another example is found in U.S. Pat. No. 5,836,030 issued to Hazeu et al. on Nov. 17, 1998. Hazeu et al. describes a motorized electric toothbrush having a removable brush attachment with linkages designed to induce specific bristle motions. None of these designs includes an automatic mode of operation that provides for motorized operation only when the toothbrush is being used by an operator.

Accordingly, it is desirable to provide an improved motorized electric toothbrush that overcomes the above referenced shortcomings of prior art toothbrushes, by providing an automatic mode of operation in which the motor engages when the toothbrush is being used by an operator.

SUMMARY OF THE INVENTION

One aspect of the present invention provides a motorized electric toothbrush that is operable in an automatic mode, such that the motor engages when the brush head contacts the user's teeth.

Another aspect of the invention provides a motorized electric toothbrush that is operable in an automatic mode, such that the motor only engages when pressure is exerted on the toothbrush handle.

Yet another aspect of the invention provides a motorized electric toothbrush that is operable in an automatic mode and has a removable head portion to facilitate replacement when the bristles are worn, and to allow use of the toothbrush by multiple users.

Accordingly, a motorized electric toothbrush is provided that comprises a handle portion that includes an electric motor. The handle portion is attached to a head portion, which includes a bristle head driven by the motor. A switch is provided for connecting the motor to an electric source. The switch has a first position for preventing motorized operation of the toothbrush, and a second position for effecting motorized operation of the toothbrush. The switch is automatically placed in the second position when the toothbrush is used by an operator.

Another aspect of the invention provides a motorized electric toothbrush that comprises a handle portion that includes an electric motor. The handle portion is attached to a head portion, which includes a bristle head driven by the motor. A first switch is provided for connecting the motor to an electric source. The first switch has a first position for preventing motorized operation of the toothbrush, and a second position for facilitating automatic operation of the toothbrush. The toothbrush also includes a second switch having a first position for preventing motorized operation of the toothbrush, and a second position for effecting motorized operation of the toothbrush when the first switch is in the second position. The second switch is automatically placed in the second position when the toothbrush is used by an operator.

A further aspect of the invention provides a motorized electric toothbrush having a handle portion that includes an electric motor. The handle portion is attached to a head portion, which includes a bristle head driven by the motor. A first switch is provided for connecting the motor to an electric source. The first switch has a first position for preventing motorized operation of the toothbrush, a second position for facilitating automatic operation of the toothbrush, and a third position for continuous motorized operation of the toothbrush. A second switch has a first position for preventing motorized operation of the toothbrush, and a second position for effecting motorized operation of the toothbrush when the first switch is in the second position. The second switch is automatically placed in the second position when the toothbrush is used by an operator.

The above object and other objects, features, and advantages of the present invention are readily apparent from the following detailed description of the best modes for carrying out the invention when taken in connection with the accompanying drawings.

BRIEF DESCRIPTION OF THE DRAWINGS

FIG. 1 shows a simplified descriptive view of a motorized electric toothbrush in accordance with the present invention;

FIG. 2 shows a simple wiring schematic for the toothbrush shown in FIG. 1;

FIG. 3 shows a simple wiring schematic for a toothbrush that includes a three position switch;

FIG. 4 shows a simple wiring schematic for a toothbrush with only one switch;

FIG. 6 shows an alternative configuration for the contact plates shown in FIG. 5;

FIG. 7 shows the contact plates of FIG. 6 when a force is applied to the bristle head of the toothbrush;

FIG. 8 shows the contact plates of FIG. 6 when the force applied to the bristle head exceeds a predetermined level;

FIG. 13 shows a partially exploded perspective view of a portion of a toothbrush in accordance with a third embodiment of the invention;

FIG. 14 shows a sectional view of a portion of the toothbrush shown in FIG. 13;

FIG. 15 shows a perspective view of a toothbrush having a one-piece compressible portion in the handle;

FIG. 16 shows a perspective view of a toothbrush having a two-piece compressible portion in the handle;

FIG. 17 shows a simplified descriptive view of a toothbrush in accordance with a fourth embodiment of the present invention;

FIG. 18 shows an enlarged detail of a switch shown in FIG. 17, the switch being shown in a first position;

FIG. 19 shows the switch from FIG. 18 in a second position;

FIG. 20 shows a simplified descriptive view of a toothbrush in accordance with a fifth embodiment of the present invention;

FIG. 21 shows a simplified descriptive view of a toothbrush in accordance with a sixth embodiment of the present invention;

FIG. 22 shows a simplified descriptive view of a toothbrush in accordance with a seventh embodiment of the present invention; and FIG. 23 shows a wiring schematic for a circuit that can be used with the toothbrush shown in FIG. 22.

DETAILED DESCRIPTION OF THE PREFERRED EMBODIMENT(S)

Figure 5:
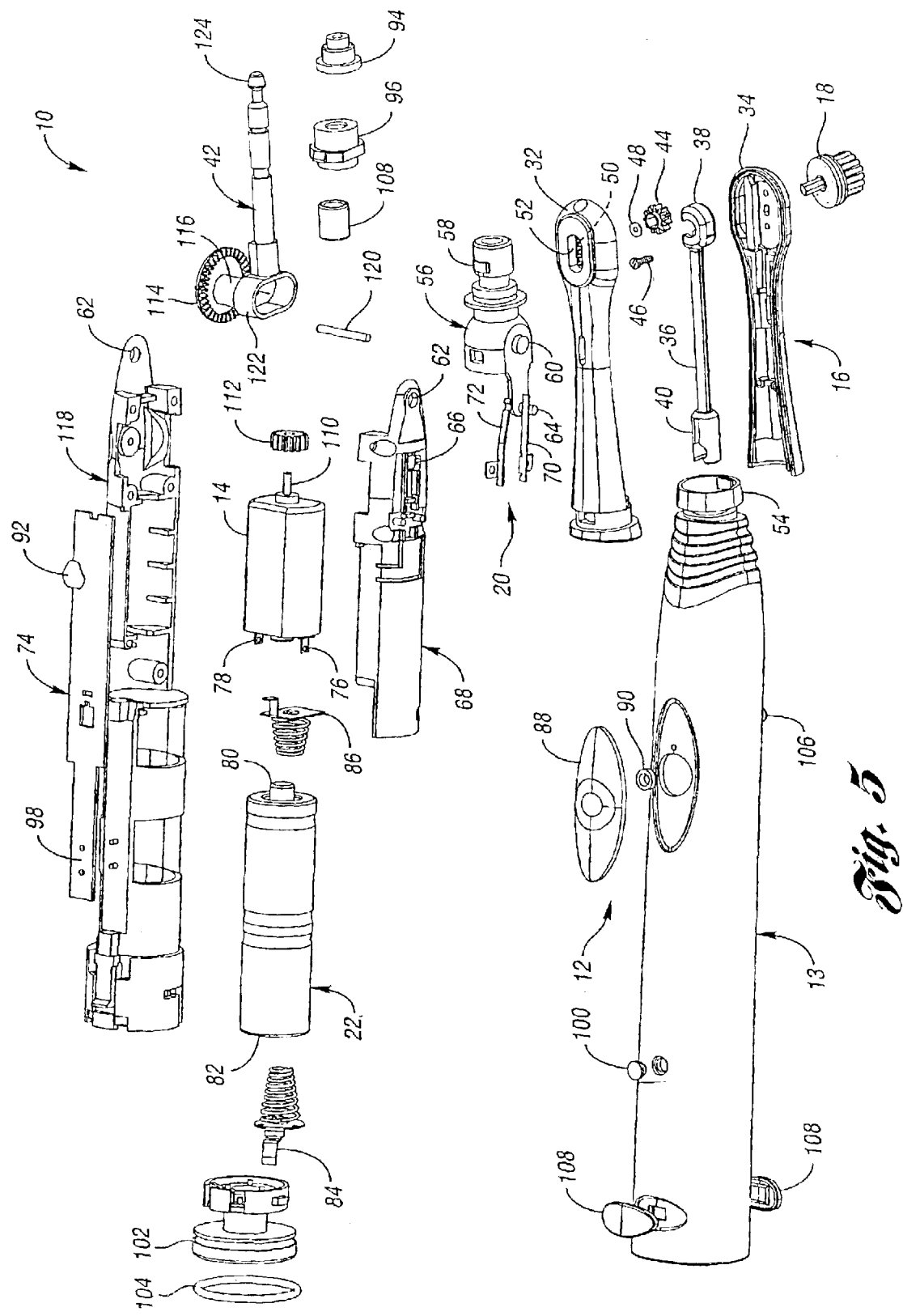
FIG. 5 shows an exploded view of the toothbrush shown in FIG. 1.
Figures 9, 10:
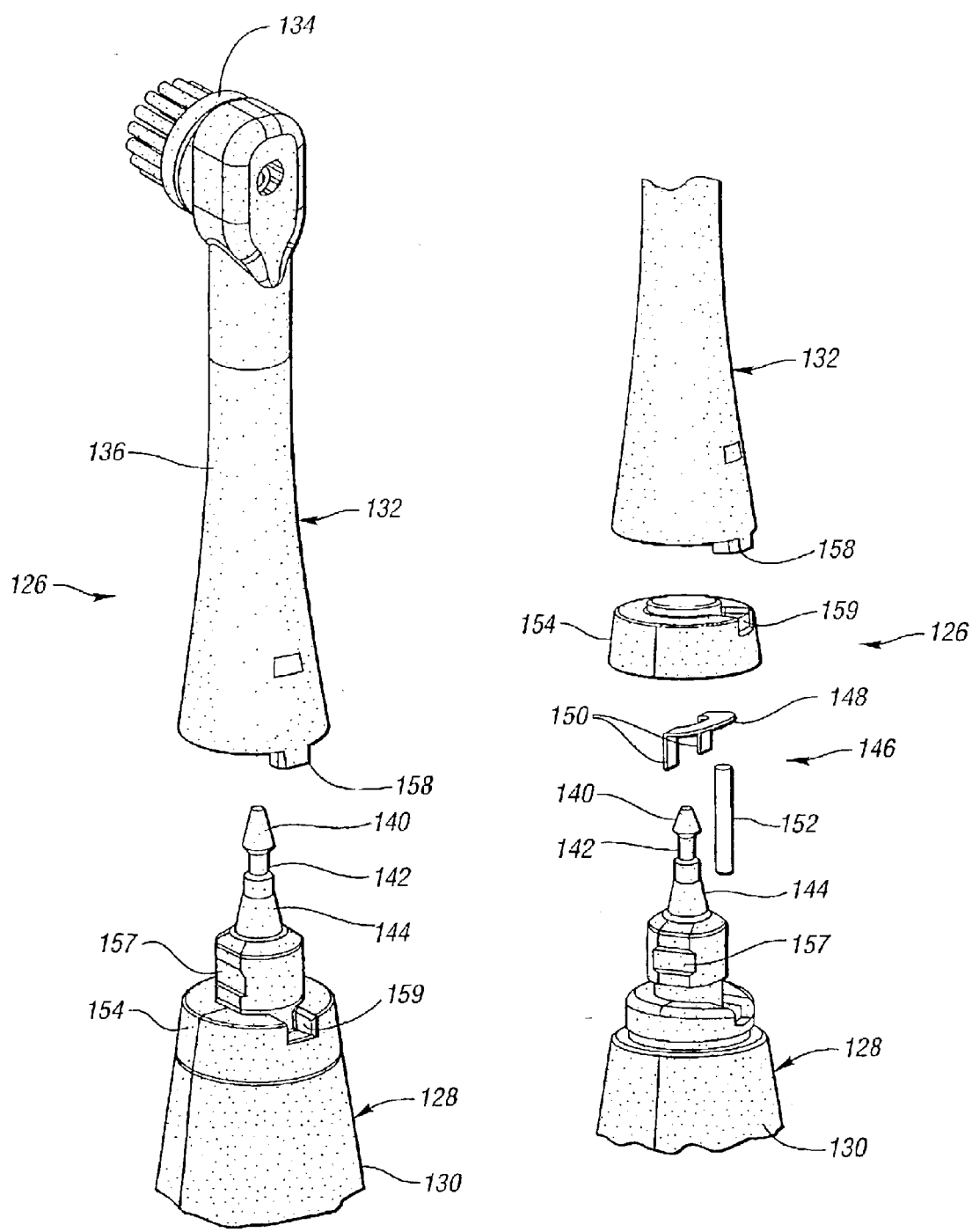
FIG. 9 shows a perspective view of a portion of a toothbrush in accordance with a second embodiment of the invention.
FIG. 10 shows a partially exploded perspective view of a portion of the toothbrush shown in FIG. 9.

FIG. 1 shows a simplified descriptive side view of a motorized electric toothbrush 10 in accordance with the present invention. A first switch 12, located in a handle portion 13, has a first or "off" position, and a second or "automatic" position, which places the toothbrush 10 in an automatic mode. While the toothbrush 10 is in the automatic mode, a motor 14 is engaged only when a force (F) is exerted on a removable head portion 16. This occurs when a bristle head 18 sufficiently contacts an operator's teeth. As used here and throughout, the term "sufficiently contacts" implies a contact that is sufficient to cause a slight movement of at least a part of the removable head portion 16 in the direction of the force. The force exerted by an operator (a user of the toothbrush) during normal brushing typically constitutes a sufficient contact. Thus, as the user begins brushing, a second switch 20 automatically moves from a first position to a second position, an electric circuit is completed, and current flows from a battery 22 to the motor 14. To drive the bristle head 18, the motor 14 transmits power to the removable head portion 16 through a series of mechanical linkages, shown in detail in FIG. 5 and partially represented in FIG. 1 as drive 24.

FIG. 2 shows a simple wiring schematic 26 of a circuit for the toothbrush 10 shown in FIG. 1. The motor 14 is electrically connected between an electric source (the battery 22) and the first switch 12. When the first switch 12 is in the first, or "off" position, the circuit 28 is open and there is no voltage across the motor 14. When the first switch 12 is in the second, or "automatic" position, control of the current flow to the motor 14 is transferred to the second switch 20. While the toothbrush 10 is in the automatic mode, the motor 14 is only engaged when a force (such as (F) shown in FIG. 1) is applied to the bristle head 18. An exception to this occurs when the toothbrush is programmed with a "delayed off" feature, discussed in more detail below. With the delayed off feature, the motor 14 continues to operate for a short time after the force is removed from the bristle head 18.

A number of alternative electrical circuits can be used with the present invention, two of which are shown in FIGS. 3 and 4. In FIG. 3, a wiring schematic 26' shows a motor 14' wired between a battery 22' and a first switch 12'. The first switch 12' is a three position switch, having a first position in which circuits 28', 30 are both open. While the first switch 12' is in the first position, no current can flow to the motor 14', and motorized operation of the toothbrush is prevented. The first switch 12' has a second position in which control of the current flow to the motor 14' is transferred to a second switch 20'. When the second switch 20' is in a first position, the circuit 28' is open, and motorized operation of the toothbrush is prevented. When a force is applied to a bristle head of the toothbrush, the second switch 20' automatically moves to a second position such that the circuit 28' is closed and the motor 14' is engaged. The first switch 12' also has a third position, in which the circuit 30 is closed, and the toothbrush operates continuously.

Yet another wiring configuration is illustrated in the wiring schematic 26" shown in FIG. 4. In this configuration, there is only one switch 20" to control the flow of current from a battery 22" to a motor 14". When the switch 20" is in a first position, circuit 28" is open, thereby preventing motorized operation of the toothbrush. When the switch 20" is in a second position, the circuit 28" is closed and current flows to the motor 14". As in the previous wiring configurations, the switch 20" automatically moves from the first position to the second position when a force is applied to a bristle head of the toothbrush. As described above, each of the switches 20, 20', and 20" "automatically" moves from a first position to a second position when the toothbrush is used by an operator. This implies that the user need not manually place the switch in the second position. Rather, the contact between the user's teeth and the bristle head automatically places the switch 20, 20', or 20" in the second position.

Toothbrushes in accordance with the present invention can be configured such that applying a force to the handle portion, rather than the bristle head, effects motorized operation of the toothbrush when it is in the automatic mode. For example, any of the switches 20, 20', 20" can be positioned within the handle portion 13 of the toothbrush 10, shown in FIG. 1. In such a case, the switch may be automatically moved from the first position to the second position not by a force applied to the bristle head 18, but rather, by a force applied to some part of the handle portion 13. Embodiments of the invention utilizing this feature are described in more detail below.

Each of the wiring configurations shown in FIGS. 2–4 allow a toothbrush to be used in an automatic mode. That is, the toothbrush motor is engaged whenever a force is applied to that portion of the toothbrush that contains the switch 20, 20', or 20". This facilitates ease of use, eliminating the need to operate a typical button switch after the bristle head is placed in the user's mouth. Another advantage of such a configuration is that a consumer can engage the toothbrush motor while the toothbrush is still packaged—i.e., prior to sale. In this way, the consumer can evaluate the operation of the toothbrush before purchase. Some prior art toothbrushes have a multi-function switch configured such that the consumer operates the toothbrush in the package using one activation mode, then operates the toothbrush during normal use in another activation mode. Such is not the case with the present invention, which affords the consumer the opportunity to activate the toothbrush in the package substantially as it will be activated during normal use. In today's consumer savvy environment, this feature provides another advantage over prior art toothbrushes.

FIG. 5 shows an exploded view of the motorized electric toothbrush 10 in accordance with one embodiment of the present invention. The toothbrush 10 includes the handle portion 13 and the removable head portion 16, which is shown having first and second housing elements 32, 34. The handle portion 13 will usually be made from a polymeric material, and may be opaque, clear, or translucent. When the handle portion 13 is clear or translucent, the toothbrush operator may see the movement of some of the toothbrush components when the motor 14 is engaged. In addition, aesthetically pleasing features such as flashing lights (not shown) can be added to the components within the handle portion 13 to augment the visual appearance. The removable head portion 16 also includes a shaft 36 that on one end has a pinion carrier 38 and on the other a yoke 40 configured to attach to a drive shaft 42. A pinion 44 is attached to the bristle head 18 with a threaded fastener 46 and a washer 48. The pinion 44 interfaces with a rack 50, only a portion of which is visible through an opening 52 in the first housing element 32. Also included in the removable head portion 16 is a snap ring 54 that is manufactured in different colors such that removable brush heads belonging to different users can have different colored snap rings for easy identification.

This embodiment of the present invention includes a rocker element 56, which serves a number of functions. First, it contains clips 58 (only one of which is visible in this view) that help secure the removable head portion 16 to the handle portion 13. In addition, trunnions 60 (only one of which is visible), rotate in apertures 62 thereby allowing the rocker element 56 to pivot as force is applied to the removable head portion 16. As the rocker element 56 pivots about the trunnions 60, a pin 64 moves within a slot 66. The slot 66 is located in a first casing portion 68 which also contains one of the apertures 62 in which one of the trunnions 60 rotates. Also located in the first casing portion 68 is the second switch 20, which comprises first and second contact plates 70, 72. As noted above, the first switch 12 is optional (see FIG. 4), in which case, the toothbrush 10 will always be in the automatic mode.

The contact plates 70, 72 are attached to the first casing portion 68 in such a way that movement of the pin 64 within the slot 66 selectively causes the contact plates 70, 72 to contact each other and electrically connect. Electrically connecting the contact plates 70, 72 places the second switch 20 is in the second position. This means that when the toothbrush 10 is in the automatic mode of operation—i.e., when the first switch 12 is in the second position—electrical connection of the contact plates 70, 72 engages the motor 14 and causes movement of the bristle head 18. Thus, when the toothbrush 10 is in the automatic mode of operation, sufficient contact of the bristle head 18 with the user's teeth will cause a slight deflection of the removable head portion 16. This in turn causes the rocker element 56 to pivot on its trunnions 60, thereby moving the pin 64 within the slot 66. When the pin 64 causes electrical connection of the contact plates 70, 72, the motor 14 is engaged without the user having to manually actuate any switches. Hence, motorized operation of the toothbrush 10 is "automatic". The contact plate 70 also acts like a spring, so that when the bristle head 18 is not in contact with the user's teeth, the contact plate 70 pushes against the pin 64 and biases away from the contact plate 72. Thus, the second switch 20 returns to the first position when the bristle head 18 is no longer in contact with the user's teeth.

Although the second switch 20 returns to the first position when the bristle head 18 is no longer in contact with the user's teeth, the motor 14 may not immediately disengage. The action of the motor 14 in this situation is dependent upon the configuration of a printed circuit (PC) board 74. The PC board 74 is an electronic controller that controls the electrical components of the toothbrush 10. The PC board 74 can be configured such that the motor 14 continues to operate for a finite time after the second switch 20 is moved from the second position to the first position. The finite time can be a very short interval, perhaps as little as a fraction of a second. This feature may be useful when the bristle head 18 momentarily disengages contact with the user's teeth during normal brushing. During the short interval, until the time the bristle head 18 is again in contact with the user's teeth, the motor 14 will continue to run and normal brushing will continue.

Although the wires are removed from this figure for clarity, the simple wiring involved in the present invention is easily understood by one skilled in the art. The PC board 74 is wired to the motor 14 at terminals 76, 78. Similarly, battery terminals 80, 82 are wired to the PC board 74 through spring terminals 84, 86. The PC board 74 can also be configured to control other functions in addition to the "delayed off" feature. For example, the PC board 74 may not only control the delay on the motor, but also the motor speed. In addition, if lights are used in conjunction with a transparent or translucent cover, as described above, the PC board 74 can be configured to control the colors, duration, and sequence of such lights. In addition, the PC board 74 can be configured to control sound elements, either alone, or in combination with the lights.

The first switch 12 includes a switch cover 88 and a switch button 90. When an operator presses the switch cover 88 the switch button 90 contacts an electrical component 92 of the PC board 74, thereby placing the switch 12 in the second position. Further pressing of the switch cover 88 toggles the switch 12 between the first and second positions. The handle portion 13 also includes a drive shaft seal 94 and a seal support 96. The drive shaft seal 94 helps to ensure that fluid does not reach the electrical components of the toothbrush 10. The PC board 74 includes a light emitting diode (LED) 98 that is visible to a user through a translucent cover 100. The LED 98 may be used to indicate when the first switch 12 is in the second position—i.e., when the toothbrush 10 is in the automatic mode—or may be used to indicate when the battery 22 is being charged. The battery 22 is held in place by an end cap 102, that is provided with an O-ring seal 104 to further ensure that fluids do not reach the electrical components of the toothbrush 10. Also included in the handle portion 13 is a seat element 106 that allows the toothbrush 10 to be laid on a flat surface such that the bristle head 18 remains pointing upward. This helps to keep the toothbrush 10 stationary on a surface that is not level, and keeps the bristle head 18 from contacting the surface. Aesthetic features 108 are added to enhance the visual appeal of the toothbrush 10.

The reciprocating movement of the drive shaft 42 is guided by a bushing 108. The actual movement of the drive shaft 42 resembles a typical slider crank mechanism. The motor 14 has a rotating motor shaft 110 that has a spur gear 112 attached to it. The spur gear 112 intermeshes with and rotates a ring gear 114 that has integrally attached to it a cam 116. The ring gear 114 and the cam 116 are held in a second casing portion 118 with a pin 120. The cam 116 rotates within a cam follower 122 that is attached to the drive shaft 42. Thus, the rotational motion of the motor shaft 110 is translated into reciprocating motion of the drive shaft 42. When the removable head portion 16 is attached to the handle portion 13, the yoke 40 connects to a head 124 on the drive shaft 42 such that the shaft 36 reciprocates along with the drive shaft 42. This in turn moves the pinion 44 along the rack 50 which causes the bristle head 18 to translate and rotate simultaneously.

An alternative configuration for the second switch 20 is shown in FIGS. 6–8. This configuration provides for automatically stopping motorized operation of the toothbrush when the force on the bristle head in response to contact with the operator's teeth exceeds a predetermined level. FIG. 6 shows a portion of a rocker element 101 that pivots about trunnions 103 (only one of which is visible). A first contact plate 105 is attached to the rocker element 101 with a fastener 107. A second contact plate 109 is attached to a casing with another fastener 107, a portion of the casing being shown as 111. The casing has a stop block 113 integrally formed therewith. The rocker element 101 includes an electrically conductive contact pad 115, which is an option that can be used when the first switch is a three-position switch (see FIG. 2). As illustrated in FIG. 6, the contact pad 115 is electrically connected to the contact plate 105, and when a three-position first switch is used, the contact pad 115 will be wired to the first switch. Thus, when the first switch is in the third position, the toothbrush motor (such as 14 shown in FIG. 2) will operate continuously. A spring 117 is disposed between the rocker element 101 and another portion of the casing (not shown), and biases the first contact plate 105 away from the second contact plate 109.

FIG. 7 is illustrative of automatic operation of the toothbrush. As the bristle head contacts the operator's teeth, the rocker element 101 pivots about the trunnions 103, thereby electrically connecting the contact plates 105, 109. As illustrated in FIGS. 6–8, the first contact plate 105 is wired to the toothbrush motor, and the second contact plate 109 is wired to the battery. Thus, when the first switch is in the second position, or when there is only one switch (see FIG. 3), the electrical connection of the contact plates 105, 109 causes motorized operation of the toothbrush. If the operator continues to apply force to the bristle head beyond a predetermined level, the first contact plate 105 will impinge on stop block 113, but the rocker element 101 will continue to pivot (see FIG. 8). A protrusion 119 on the rocker element 101 then contacts the second contact plate 109 and pushes it away from the first contact plate 105. This opens an electric circuit and stops the toothbrush motor. Even if the toothbrush has a "continuous on" feature, the motor will still stop when the first contact plate 105 impinges on the stop block 113. This is because the contact pad 115 will no longer be in contact with the first contact plate 105. The predetermined level at which the motor is stopped can be easily adjusted by changing the spring 117, the size of the stop block 113, or the size of the protrusion 119.

FIGS. 9–13 show portions of a toothbrush 126 in accordance with another embodiment of the present invention. The toothbrush 126 comprises a handle portion 128 that includes a first housing 130, and a removable head portion 132 that includes a bristle head 134 and a second housing 136. In this embodiment, the drive mechanism within the removable head portion 132 is the same as in the preferred embodiment. This includes a shaft and a pinion which interfaces with a rack to drive the bristle head 134. A yoke 138, seen in FIGS. 11 and 12, connects to a head 140 of a drive shaft 142 which reciprocates when a motor (not shown) is engaged. A seal 144 is disposed around the drive shaft 142 to protect the electrical components of the toothbrush 126 from contamination by fluids.

As in the previous embodiment, the toothbrush 126 includes an automatic mode of operation. To facilitate the automatic mode of operation, the toothbrush 126 has a first switch (not shown) that is configured as in the previous embodiment. A second switch 146, seen in FIGS. 10 and 12, includes a contact plate 148 having legs 150 and a contact rod 152. The contact plate 148 and the contact rod 152 are disposed within the handle portion 128 and are covered by a seal 154. Similar to the contact plates 70, 72 used in the first embodiment, the contact plate 148 and the contact rod 152 are wired to a PC board (not shown).

Figure 11:
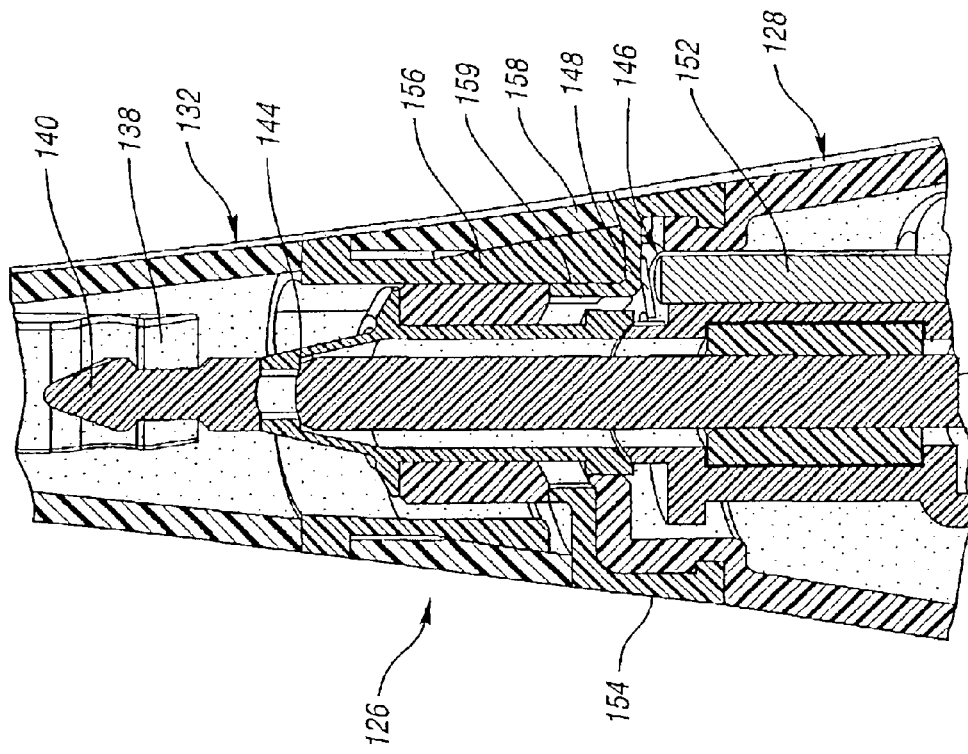
FIG. 11 shows a sectional view of a portion of the toothbrush shown in FIG. 9.
Figure 12:
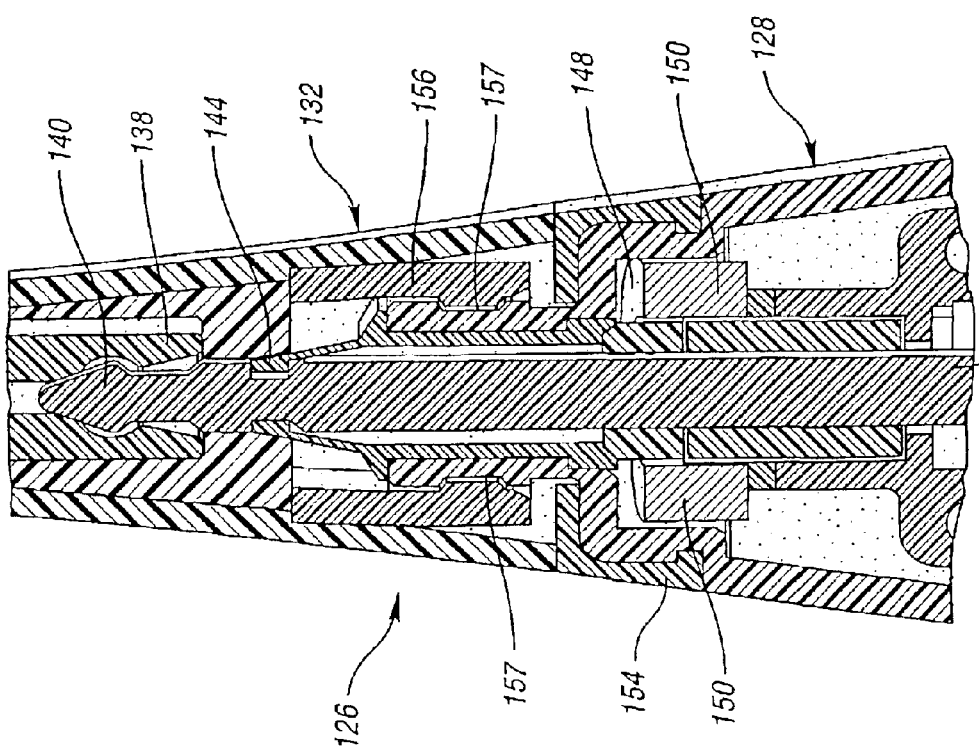
FIG. 12 shows another sectional view of the toothbrush shown in FIG. 9.

The method by which the removable head portion 132 attaches to the handle portion 128 is also different from the first embodiment. An adaptor 156, seen in FIGS. 11 and 12, is located inside the housing 136 of the removable head portion 132, and snaps into recesses 157 in the handle portion 128, (see FIG. 11). This attachment allows the removable head portion 132 to be securely attached to the handle portion 128, and at the same time allows the head portion 132 to pivot in relation to the handle portion 128 when the bristle head 134 sufficiently contacts the user's teeth. As consistently used throughout the various embodiments, "sufficiently contacts" merely implies a contact that is sufficient to cause a slight movement of at least a part of the removable head portion 132.

As the removable head portion 132 undergoes the slight pivoting motion caused by contact with the user's teeth, a projection 158 pushes into a notch 159 in the seal 154. As the projection 158 moves into the notch 159, it pushes the seal 154 against the contact plate 148. With the legs 150 held stationary, the contact plate 148 deflects in a spring-like fashion until it contacts the contact rod 152. This places the second switch 146 in the second position, and allows for motorized operation of the toothbrush 126 when it is in the automatic mode. The spring-like deflection of the contact plate 148 also acts to bias it away from the contact rod 152, to disengage the motor when the bristle head is not in contact with the user's teeth. As in the previous embodiment, the PC board can be configured such that the motor does not disengage immediately, but rather, remains engaged for a short time after the bristle head is removed from the user's teeth.

Although both of the embodiments described above have a two-position first switch, as illustrated schematically in FIG. 2, a three-position switch (as shown in FIG. 3) can be used. Alternatively, the first switch can be eliminated, as in FIG. 4, so that the toothbrush is always in the automatic mode. The two toothbrushes described above include removable brush head portions; however, either can be made with a non-removable brush head portion. In fact, any of the embodiments described herein can be made with a non-removable brush head portion, which may be particularly well suited to disposable toothbrush designs.

Portions of a third embodiment of the present invention are shown in FIGS. 13 and 14. In this embodiment, a toothbrush 160 includes a handle portion 162 that has a first housing 163, and a removable head portion 164 that has a second housing 165 and a bristle head (not shown). As in the previous embodiments, the toothbrush 160 includes a first switch (not shown) having a first, or "off" position that prevents motorized operation of the toothbrush 160, and a second, or "automatic" position that allows the toothbrush 160 to function in an automatic mode. A second switch 166 comprises first and second stationary contact plates 168, 170, and a third contact plate 172. The removable head portion 164 includes a projection 174 that fits into a notch 176 in the first housing 163 of the handle portion 162.

The removable head portion 164 attaches to the handle portion 162 at snaps 178. This connection allows the removable head portion 164 be securely attached to the handle portion 162, and at the same time allows the head portion 164 to pivot in relation to the handle portion 162 when a bristle head (not shown) sufficiently contacts the user's teeth. As the removable head portion 164 pivots, the third contact plate 172 contacts, and thereby electrically connects, the stationary contact plates 168, 170. This places the second switch 166 in the second position, and causes motorized operation of the toothbrush 160 when it is in the automatic mode. The projection 174 also acts as a spring as the removable head portion 164 pivots, thereby keeping the third plate 172 biased away from the stationary plates 168, 170 when the bristle head is not in contact with the user's teeth.

In each of the embodiments described above, the second switch was automatically moved from the first position to the second position when a force was applied to the bristle head. Specifically, a force on the bristle head in response to its contact with the operator's teeth caused the second switch to move to the second position and the motor was engaged. As previously noted however, the second switch need not be activated by a force on the bristle head. Rather, the second, switch may be located such that it is automatically placed in the second position when the user grips the handle portion. One way to accomplish this is to provide the handle portion with a compressible portion, and dispose the second switch in relation to the compressible portion such that compressing the compressible portion moves the second switch from the first position to the second position, thereby engaging the motor.

FIGS. 15 and 16 illustrate two embodiments of toothbrushes having differently configured handle portions. FIG. 15 illustrates a toothbrush 180 having a compressible portion 182. The compressible portion 182 can be molded integrally with toothbrush handle housing 184, or may be attached in a separate operation. The compressible portion 182 is typically made from a polymeric material that deflects when the toothbrush is used in a normal brushing operation. The handle housing 184 may be configured with a relatively small, or a relatively large compressible portion. In this embodiment, the compressible portion 182 occupies a large area of the handle housing 184, thereby helping to ensure that users having different gripping preferences will be accommodated.

FIG. 16 illustrates a toothbrush 186 having a compressible portion 188 located in a housing 190 of a handle portion 192. In this embodiment, the compressible portion 188 includes a rigid portion 194 and a non-rigid portion 196. When a user compresses the compressible portion 188, the non-rigid portion deflects, thereby moving a switch (not shown) from a first position to a second position to effect motorized operation of the toothbrush 186. Having a two-piece compressible portion such as 188 not only changes the look, but also the feel of the toothbrush when compared to a toothbrush having a single piece compressible portion. Thus, the designer is allowed flexibility with regard to both form and function.

FIG. 17 shows a toothbrush 198 that includes a removable head portion 200 and a handle portion 202. The handle portion 202 includes a first switch 204 which has first and second positions for respectively preventing and facilitating motorized operation of the toothbrush 198. The handle portion 202 includes a handle housing 206 that has a compressible portion 208. Disposed within the handle portion 202 in close proximity to the compressible portion 208, is a second switch 210, shown in detail in FIG. 18.

The switch 210 shown in FIG. 18 includes a magnet 212, a magnetic plate 214, and a non-magnetic plate 216. When the first switch 204 is in the second position, motorized operation of the toothbrush 198 occurs only when a force (F) is exerted on the compressible portion 208. This force causes the magnet 212 to move in close proximity to the magnetic and non-magnetic plates 214, 216. When the distance between the magnet 212 and the magnetic plate 214 drops below a fixed distance 218, the two plates 214, 216 contact each other (see FIG. 19). When the first switch 204 is in the second position, and the two plates 214, 216 contact each other, a motor (not shown) is engaged, thereby causing movement of the bristle head 220.

FIG. 20 shows a fifth embodiment of a toothbrush 222 in accordance with the present invention. The toothbrush 222 has a handle portion 224 and a removable head portion 226. The handle portion 224 includes a compressible portion 228. Unlike previous embodiments, the toothbrush 222 only has one switch 229 which comprises a magnet 230 and a Hall effect sensor 232. The magnet 230 is located beneath the compressible portion 228, and application of force (F) to the compressible portion 228 causes the distance between the magnet 230 and the Hall effect sensor 232 to decrease. When this distance is small enough, current flows through the Hall effect sensor 232, and the motor (not shown) is engaged.

FIG. 21 shows a sixth embodiment of the present invention. A toothbrush 234 includes a handle portion 236 and a removable head portion 238. As in the fifth embodiment, the toothbrush 234 includes only one switch 240. The switch 240 comprises first and second contact plates 242, 244 located beneath a compressible portion 246. When a force (F) is applied to the compressible portion 246, the contact plates 242, 244 are moved closer to each other until they contact, thereby placing the switch in the second position and causing motorized operation of the toothbrush 234.

FIG. 22 illustrates another embodiment of a motorized electric toothbrush 248 in accordance with the present invention. The toothbrush 248 has a handle portion 250 and a removable head portion 252. The handle portion 250 includes a first switch 254 and a sensing device. The sensing device includes a capacitive sensor 255 attached to a pair of tactile sensors 256, 258. As explained in conjunction with the wiring schematic 260 shown in FIG. 23, the mere presence of a user's hand on the tactile sensors 256, 258 will effect motorized operation of the toothbrush 248, when the first switch 254 is in the second position. When a user's hand contacts the tactile sensors 256, 258, the switch 262 moves from a first position to a second position. If the first switch 254 is also in the second position, current will flow from the battery 264 to the motor 266. As with the previous embodiments, the first switch 254 can be eliminated; thus, the toothbrush 248 will always be in an automatic mode and the presence of the user's hand on tactile sensors 256, 258 will always effect motorized operation of the toothbrush 248.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A motorized electric toothbrush, comprising:

a handle portion;

an electric motor disposed within the handle portion;

a head portion attached to the handle portion, the head portion including a bristle head driven by the motor;

a switch for connecting the motor to an electric source, the switch having a first position for preventing motorized operation of the toothbrush, a second position for effecting motorized operation of the toothbrush, and a third position for automatically stopping motorized operation of the toothbrush, the switch being placed in the second position when a force is exerted on the bristle head in response to contact with an operator's teeth, and the switch being placed in the third position when the force on the bristle head exceeds a predetermined level; and an electronic controller configured to facilitate operation of the motor for a finite time after the switch is moved from the second position to the first position.

2. A motorized electric toothbrush, comprising:

a handle portion;

an electric motor disposed within the handle portion;

a head portion attached to the handle portion, the head portion Including a bristle head driven by the motor;

a first switch for connecting the motor to an electric source, the first switch having a first position for preventing motorized operation of the toothbrush and a second position for facilitating automatic operation of the toothbrush;

a second switch having a first position for preventing motorized operation of the toothbrush, a second position for effecting motorized operation of the toothbrush when the first switch is in the second position, and a third position for automatically stopping motorized operation of the toothbrush, the second switch being placed in the second position when a force is exerted on the bristle head in response to contact with an operator's teeth, and the second switch being placed in the third position when the force on the bristle head exceeds a predetermined force; and an electronic controller configured to facilitate operation of the motor for a finite time after the second switch is moved from the second position to the first position.

3. The electric toothbrush as in any of the preceding claims, wherein the head portion is removable from the handle portion.

4. The electric toothbrush of claim 2, wherein the second switch comprises first and second contact plates disposed to electrically connect, thereby placing the second switch in the second position when the bristle head sufficiently contacts the operator's teeth.

5. The electric toothbrush of claim 4, further comprising a rocker element disposed in the handle portion and pivotally supported on at least one trunnion, the rocker element being configured to selectively bring the first and second contact plates into contact with each other, to place the second switch in the second position when a force is applied to the bristle head in response to contact with an operator's teeth.

6. The electric toothbrush of claim 2, wherein the second switch includes first and second contact plates, the toothbrush further comprising a rocker element disposed in the handle portion and pivotally supported on at least one trunnion, the rocker element being configured to selectively bring the first and second contact plates into contact with each other, to place the second switch in the second position when a force is applied to the bristle head in response to contact with an operator s teeth.

7. The electric toothbrush of claim 2, wherein the first switch includes a third position for continuous motorized operation of the toothbrush.

8. The electric toothbrush of claim 1, wherein the switch includes first and second contact plates, the toothbrush further comprising a rocker element disposed in the handle portion and pivotally supported on at least one trunnion, the rocker element being configured to selectively bring the first and second contact plates into contact with each other, to place the switch in the second position when a force is applied to the bristle head in response to contact with an operator's teeth.

* * * * *